(12) United States Patent
Malkowski

(10) Patent No.: US 9,357,984 B2
(45) Date of Patent: Jun. 7, 2016

(54) CONSTANT VALUE GAP STABILIZER FOR ARTICULATING LINKS

(71) Applicant: Covidien LP, Mansfield, MA (US)

(72) Inventor: Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 93 days.

(21) Appl. No.: 14/247,275

(22) Filed: Apr. 8, 2014

(65) Prior Publication Data

US 2014/0316432 A1    Oct. 23, 2014

Related U.S. Application Data

(60) Provisional application No. 61/814,875, filed on Apr. 23, 2013.

(51) Int. Cl.
*A61B 17/00* (2006.01)
*A61B 17/34* (2006.01)

(52) U.S. Cl.
CPC ....... *A61B 17/00234* (2013.01); *A61B 17/3421* (2013.01); *A61B 17/3423* (2013.01); *A61B 2017/00305* (2013.01); *A61B 2017/00314* (2013.01); *A61B 2017/00323* (2013.01)

(58) Field of Classification Search
CPC ............ A61B 17/00234; A61B 17/3421; A61B 17/3423; A61B 2017/00305; A61B 2017/00314; A61B 2017/00323; A61B 2017/22071; A61B 1/005; A61B 1/008; A61B 1/0051; A61B 1/0055; A61B 1/0056; A61B 1/0054; A61B 1/0053; A61B 1/0052; A61B 17/28; A61B 17/29; A61B 17/10; A61B 17/11; A61B 17/068; A61B 17/115; A61B 17/1114; A61B 2017/2901; A61B 2017/2905; A61B 2017/2908; A61B 2017/1125; A61B 2017/1157; A61M 25/0105; A61F 5/0043; A61F 5/0046; A61F 5/0083; A61F 5/0086
USPC ......................................................... 600/184
See application file for complete search history.

(56) References Cited

U.S. PATENT DOCUMENTS

| | | | |
|---|---|---|---|
| 2,028,635 A | 1/1936 | Wappler |
| 2,507,710 A | 5/1950 | Grosso |
| 2,790,437 A | 4/1957 | Moore |
| 3,071,161 A | 1/1963 | Ulrich |
| 3,162,214 A | 12/1964 | Bazinet |
| 3,190,286 A | 6/1965 | Stokes |
| 3,557,780 A | 1/1971 | Sato |
| 3,858,577 A | 1/1975 | Bass et al. |
| 3,892,228 A | 7/1975 | Mitsui |
| 3,895,636 A | 7/1975 | Schmidt |
| 4,066,071 A | 1/1978 | Nagel |

(Continued)

FOREIGN PATENT DOCUMENTS

| | | |
|---|---|---|
| EP | 0095970 A2 | 12/1983 |
| EP | 0448284 A2 | 9/1991 |

(Continued)

*Primary Examiner* — Jonathan W Miles
*Assistant Examiner* — George J Ulsh

(57) ABSTRACT

A surgical instrument is adapted and configured for use in a minimally invasive surgical procedure. The surgical instrument includes at least one pair of segments including a plurality of articulating links having gaps therebetween. At least one gap stabilizer stabilizes the articulating links and facilitates maintaining equally sized gaps between the articulating links during bending of the surgical instrument.

15 Claims, 11 Drawing Sheets

(56) References Cited

U.S. PATENT DOCUMENTS

| | | |
|---|---|---|
| 4,351,323 A | 9/1982 | Ouchi et al. |
| 4,432,349 A | 2/1984 | Oshiro |
| 4,483,562 A | 11/1984 | Schoolman |
| 4,530,568 A | 7/1985 | Haduch et al. |
| 4,655,257 A | 4/1987 | Iwashita |
| 4,669,471 A | 6/1987 | Hayashi |
| 4,674,230 A | 6/1987 | Takeo et al. |
| 4,686,963 A | 8/1987 | Cohen et al. |
| 4,688,554 A | 8/1987 | Habib |
| 4,688,555 A | 8/1987 | Wardle |
| 4,728,020 A | 3/1988 | Green et al. |
| 4,763,669 A | 8/1988 | Jaeger |
| 4,773,395 A | 9/1988 | Suzuki et al. |
| 4,796,607 A | 1/1989 | Allred, III et al. |
| 4,832,473 A | 5/1989 | Ueda |
| 4,846,573 A | 7/1989 | Taylor et al. |
| 4,872,456 A | 10/1989 | Hasson |
| 4,880,015 A | 11/1989 | Nierman |
| 4,944,093 A | 7/1990 | Falk |
| 4,944,741 A | 7/1990 | Hasson |
| 4,945,920 A | 8/1990 | Clossick |
| 4,950,273 A | 8/1990 | Briggs |
| 4,982,727 A | 1/1991 | Sato |
| 5,002,543 A | 3/1991 | Bradshaw et al. |
| 5,035,248 A | 7/1991 | Zinnecker |
| 5,042,707 A | 8/1991 | Taheri |
| 5,080,663 A | 1/1992 | Mills et al. |
| 5,100,430 A | 3/1992 | Avellanet et al. |
| 5,133,727 A | 7/1992 | Bales et al. |
| 5,137,013 A | 8/1992 | Chiba et al. |
| 5,152,779 A | 10/1992 | Sanagi |
| 5,207,114 A | 5/1993 | Salisbury, Jr. et al. |
| 5,209,747 A | 5/1993 | Knoepfler |
| 5,228,451 A | 7/1993 | Bales et al. |
| 5,238,002 A | 8/1993 | Devlin et al. |
| 5,254,130 A | 10/1993 | Poncet et al. |
| 5,271,381 A | 12/1993 | Ailinger et al. |
| 5,275,608 A | 1/1994 | Forman et al. |
| 5,308,353 A | 5/1994 | Beurrier |
| 5,318,528 A | 6/1994 | Heaven et al. |
| 5,330,502 A | 7/1994 | Hassler et al. |
| 5,336,221 A | 8/1994 | Anderson |
| 5,344,428 A | 9/1994 | Griffiths |
| 5,354,311 A | 10/1994 | Kambin et al. |
| 5,383,880 A | 1/1995 | Hooven |
| 5,383,888 A | 1/1995 | Zvenyatsky et al. |
| 5,383,895 A | 1/1995 | Holmes et al. |
| 5,386,818 A | 2/1995 | Schneebaum et al. |
| 5,395,367 A | 3/1995 | Wilk |
| 5,403,342 A | 4/1995 | Tovey et al. |
| 5,405,344 A | 4/1995 | Williamson et al. |
| 5,411,481 A | 5/1995 | Allen et al. |
| 5,417,203 A | 5/1995 | Tovey et al. |
| 5,419,339 A | 5/1995 | Palmer |
| 5,433,721 A | 7/1995 | Hooven et al. |
| 5,439,467 A | 8/1995 | Benderev et al. |
| 5,441,494 A | 8/1995 | Ortiz |
| 5,448,989 A | 9/1995 | Heckele |
| 5,454,378 A | 10/1995 | Palmer et al. |
| 5,454,827 A | 10/1995 | Aust et al. |
| 5,462,527 A | 10/1995 | Stevens-Wright et al. |
| 5,474,571 A | 12/1995 | Lang |
| 5,480,406 A | 1/1996 | Nolan et al. |
| 5,490,861 A | 2/1996 | Kratsch et al. |
| 5,501,654 A | 3/1996 | Failla et al. |
| 5,514,157 A | 5/1996 | Nicholas et al. |
| 5,520,678 A | 5/1996 | Heckele et al. |
| 5,527,322 A | 6/1996 | Klein et al. |
| 5,535,754 A | 7/1996 | Doherty |
| 5,545,148 A | 8/1996 | Wurster |
| 5,549,617 A | 8/1996 | Green et al. |
| 5,562,686 A | 10/1996 | Sauer et al. |
| 5,569,269 A | 10/1996 | Hart et al. |
| 5,569,299 A | 10/1996 | Dill et al. |
| 5,571,136 A | 11/1996 | Weaver |
| 5,578,056 A | 11/1996 | Pauldrach |
| 5,582,617 A | 12/1996 | Klieman et al. |
| 5,591,202 A | 1/1997 | Slater et al. |
| 5,601,599 A | 2/1997 | Nunez |
| 5,607,450 A | 3/1997 | Zvenyatsky et al. |
| 5,618,294 A | 4/1997 | Aust et al. |
| 5,624,397 A | 4/1997 | Snoke et al. |
| 5,643,294 A | 7/1997 | Tovey et al. |
| 5,667,476 A | 9/1997 | Frassica et al. |
| 5,702,408 A | 12/1997 | Wales et al. |
| 5,728,107 A | 3/1998 | Zlock et al. |
| 5,728,113 A | 3/1998 | Sherts |
| 5,759,151 A | 6/1998 | Sturges |
| 5,762,067 A | 6/1998 | Dunham et al. |
| 5,766,196 A | 6/1998 | Griffiths |
| 5,772,578 A | 6/1998 | Heimberger et al. |
| 5,792,152 A | 8/1998 | Klein et al. |
| 5,810,715 A | 9/1998 | Moriyama |
| 5,810,717 A | 9/1998 | Maeda et al. |
| 5,823,066 A | 10/1998 | Huitema et al. |
| 5,827,177 A | 10/1998 | Oneda et al. |
| 5,830,220 A | 11/1998 | Wan et al. |
| 5,851,208 A | 12/1998 | Trott |
| 5,855,569 A | 1/1999 | Komi |
| 5,871,488 A | 2/1999 | Tovey et al. |
| 5,873,817 A | 2/1999 | Kokish et al. |
| 5,899,425 A | 5/1999 | Corey, Jr. et al. |
| 5,904,667 A | 5/1999 | Falwell |
| 5,908,428 A | 6/1999 | Scirica et al. |
| 5,916,147 A | 6/1999 | Boury |
| 5,919,199 A | 7/1999 | Mers Kelly et al. |
| 5,944,690 A | 8/1999 | Falwell et al. |
| 5,976,074 A | 11/1999 | Moriyama |
| 6,036,636 A | 3/2000 | Motoki et al. |
| 6,083,170 A | 7/2000 | Ben-Haim |
| 6,139,563 A | 10/2000 | Cosgrove, III et al. |
| 6,169,916 B1 | 1/2001 | West |
| 6,206,893 B1 | 3/2001 | Klein et al. |
| 6,270,453 B1 | 8/2001 | Sakai |
| 6,482,149 B1 | 11/2002 | Torii |
| 6,522,933 B2 | 2/2003 | Nguyen |
| 6,554,845 B1 | 4/2003 | Fleenor et al. |
| 6,663,588 B2 | 12/2003 | DuBois et al. |
| 6,666,854 B1 | 12/2003 | Lange |
| 6,702,737 B2 | 3/2004 | Hino et al. |
| 6,743,239 B1 | 6/2004 | Kuehn et al. |
| 6,780,151 B2 | 8/2004 | Grabover et al. |
| 6,811,532 B2 | 11/2004 | Ogura et al. |
| 6,837,849 B2 | 1/2005 | Ogura et al. |
| 6,905,461 B2 | 6/2005 | Hino |
| 6,997,931 B2 | 2/2006 | Sauer et al. |
| 7,147,650 B2 | 12/2006 | Lee |
| 7,159,750 B2 | 1/2007 | Racenet et al. |
| 7,338,513 B2 | 3/2008 | Lee et al. |
| 7,364,582 B2 | 4/2008 | Lee |
| 7,377,906 B2 | 5/2008 | Selkee |
| 7,410,483 B2 | 8/2008 | Danitz et al. |
| 7,424,965 B2 | 9/2008 | Racenet et al. |
| 7,494,039 B2 | 2/2009 | Racenet et al. |
| 7,584,880 B2 | 9/2009 | Racenet et al. |
| 7,597,230 B2 | 10/2009 | Racenet et al. |
| 7,615,066 B2 | 11/2009 | Danitz et al. |
| 7,658,708 B2 | 2/2010 | Schwartz et al. |
| 7,678,117 B2 | 3/2010 | Hinman et al. |
| 7,682,307 B2 | 3/2010 | Danitz et al. |
| 7,721,935 B2 | 5/2010 | Racenet et al. |
| 7,758,569 B2 | 7/2010 | Brock |
| 7,766,821 B2 | 8/2010 | Brunnen et al. |
| 7,785,252 B2 | 8/2010 | Danitz et al. |
| 7,793,814 B2 | 9/2010 | Racenet et al. |
| 7,861,907 B2 | 1/2011 | Green et al. |
| 7,891,533 B2 | 2/2011 | Green et al. |
| 7,909,220 B2 | 3/2011 | Viola |
| 7,914,445 B2 | 3/2011 | Smith et al. |
| 7,918,861 B2 | 4/2011 | Brock et al. |
| 7,931,616 B2 | 4/2011 | Selkee |
| 7,963,433 B2 | 6/2011 | Whitman et al. |
| 8,070,685 B2 | 12/2011 | Harhen et al. |
| 8,100,824 B2 | 1/2012 | Hegeman et al. |

(56) References Cited

U.S. PATENT DOCUMENTS

| | | |
|---|---|---|
| 8,123,703 B2 | 2/2012 | Martin et al. |
| 8,177,794 B2 | 5/2012 | Cabrera et al. |
| 8,182,418 B2 | 5/2012 | Durant et al. |
| 8,246,637 B2 | 8/2012 | Viola et al. |
| 8,252,019 B2 | 8/2012 | Fleming, III |
| 8,277,375 B2 | 10/2012 | Danitz et al. |
| 8,292,147 B2 | 10/2012 | Viola |
| 8,292,889 B2 | 10/2012 | Cunningham et al. |
| 8,292,905 B2 | 10/2012 | Taylor et al. |
| 8,313,509 B2 | 11/2012 | Kostrzewski |
| 8,323,297 B2 | 12/2012 | Hinman et al. |
| 8,328,860 B2 | 12/2012 | Strauss et al. |
| 8,337,515 B2 | 12/2012 | Viola et al. |
| 8,342,379 B2 | 1/2013 | Whitman et al. |
| 8,372,033 B2 | 2/2013 | Kronstedt et al. |
| 8,403,832 B2 | 3/2013 | Cunningham et al. |
| 2002/0062062 A1 | 5/2002 | Belson et al. |
| 2002/0095175 A1 | 7/2002 | Brock et al. |
| 2002/0128661 A1 | 9/2002 | Brock et al. |
| 2002/0133173 A1 | 9/2002 | Brock et al. |
| 2002/0177750 A1 | 11/2002 | Pilvisto |
| 2002/0177847 A1 | 11/2002 | Long |
| 2003/0045900 A1 | 3/2003 | Hahnen et al. |
| 2003/0065359 A1 | 4/2003 | Weller et al. |
| 2003/0109898 A1 | 6/2003 | Schwarz et al. |
| 2003/0135204 A1 | 7/2003 | Lee et al. |
| 2003/0149338 A1 | 8/2003 | Francois et al. |
| 2003/0216618 A1 | 11/2003 | Arai |
| 2003/0233104 A1 | 12/2003 | Gellman et al. |
| 2004/0049205 A1 | 3/2004 | Lee et al. |
| 2004/0111009 A1 | 6/2004 | Adams et al. |
| 2004/0138529 A1 | 7/2004 | Wiltshire et al. |
| 2004/0176751 A1 | 9/2004 | Weitzner et al. |
| 2004/0193146 A1 | 9/2004 | Lee et al. |
| 2004/0236316 A1 | 11/2004 | Danitz et al. |
| 2005/0049580 A1 | 3/2005 | Brock et al. |
| 2005/0107667 A1 | 5/2005 | Danitz et al. |
| 2005/0182298 A1 | 8/2005 | Ikeda et al. |
| 2005/0222558 A1 | 10/2005 | Baxter et al. |
| 2005/0228440 A1 | 10/2005 | Brock et al. |
| 2005/0251112 A1 | 11/2005 | Danitz et al. |
| 2006/0149295 A1 | 7/2006 | Fleming, III |
| 2006/0178556 A1 | 8/2006 | Hasser et al. |
| 2007/0273084 A1 | 11/2007 | Chu et al. |
| 2007/0273085 A1 | 11/2007 | Nanno et al. |
| 2008/0051631 A1 | 2/2008 | Dejima et al. |
| 2008/0262538 A1 | 10/2008 | Danitz et al. |
| 2008/0308603 A1 | 12/2008 | Shelton et al. |
| 2009/0093752 A1 | 4/2009 | Richard et al. |
| 2009/0283568 A1 | 11/2009 | Racenet et al. |
| 2010/0076260 A1 | 3/2010 | Taylor et al. |
| 2010/0076433 A1 | 3/2010 | Taylor et al. |
| 2010/0076460 A1 | 3/2010 | Taylor et al. |
| 2010/0094289 A1 | 4/2010 | Taylor et al. |
| 2010/0130823 A1 | 5/2010 | Ando |
| 2010/0179540 A1 | 7/2010 | Marczyk et al. |
| 2010/0217282 A1 | 8/2010 | Cabrera et al. |
| 2010/0261964 A1 | 10/2010 | Danitz et al. |
| 2010/0261971 A1 | 10/2010 | Danitz et al. |
| 2010/0262075 A1 | 10/2010 | Danitz et al. |
| 2010/0262161 A1 | 10/2010 | Danitz et al. |
| 2010/0262180 A1 | 10/2010 | Danitz et al. |
| 2011/0036888 A1 | 2/2011 | Pribanic et al. |
| 2011/0184459 A1 | 7/2011 | Malkowski et al. |
| 2011/0213363 A1 | 9/2011 | Cunningham et al. |
| 2011/0282149 A1 | 11/2011 | Vargas et al. |
| 2012/0035617 A1 | 2/2012 | Joshi et al. |
| 2012/0203142 A1 | 8/2012 | Bedell |
| 2012/0253116 A1 | 10/2012 | Sniffin et al. |
| 2012/0253131 A1 | 10/2012 | Malkowski et al. |
| 2012/0253325 A1 | 10/2012 | Sniffin et al. |
| 2012/0253327 A1 | 10/2012 | Malkowski |
| 2012/0277769 A1 | 11/2012 | Cabrera et al. |
| 2012/0310220 A1 | 12/2012 | Malkowski et al. |

FOREIGN PATENT DOCUMENTS

| | | |
|---|---|---|
| EP | 0626604 A2 | 11/1994 |
| GB | 2143920 A | 2/1985 |

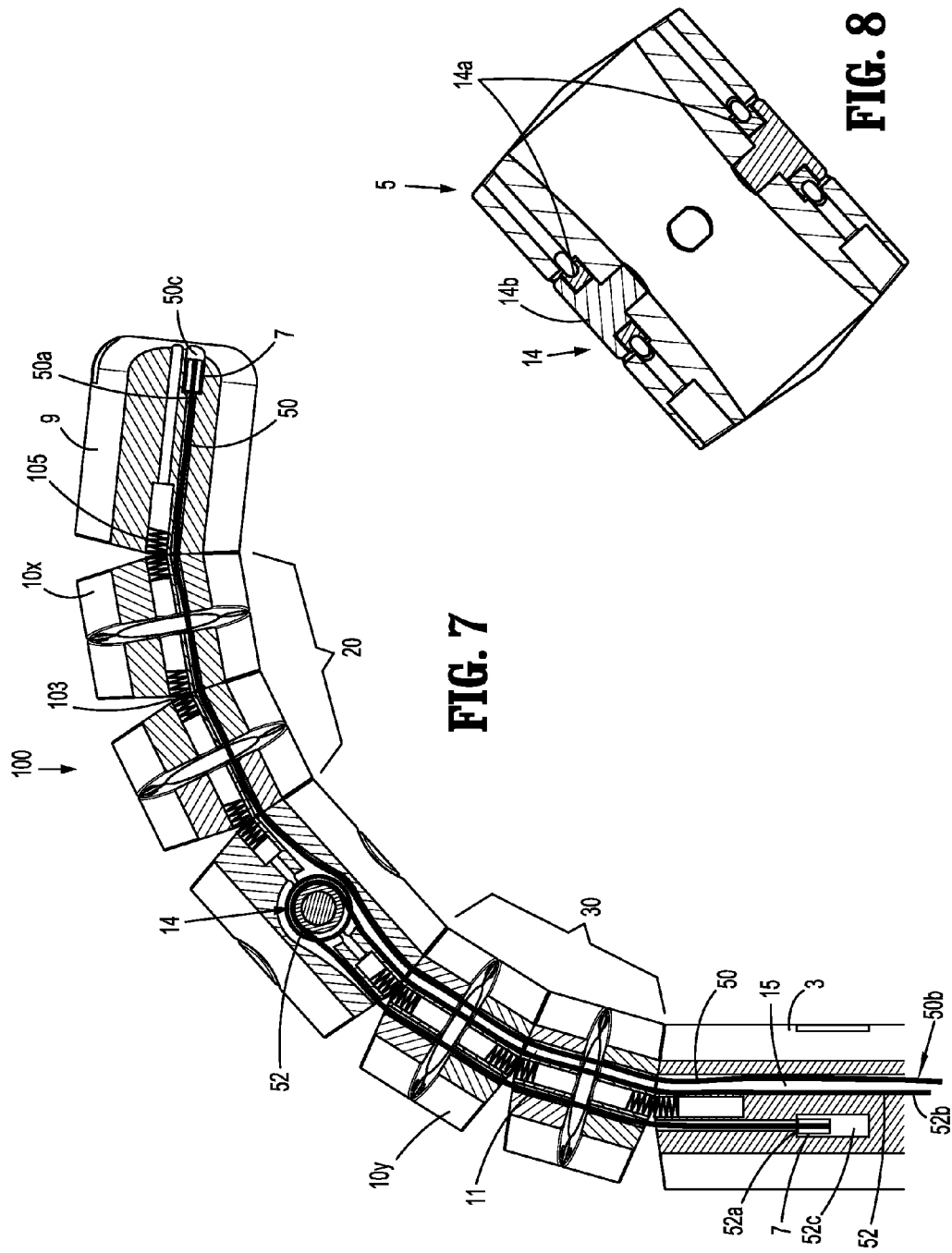

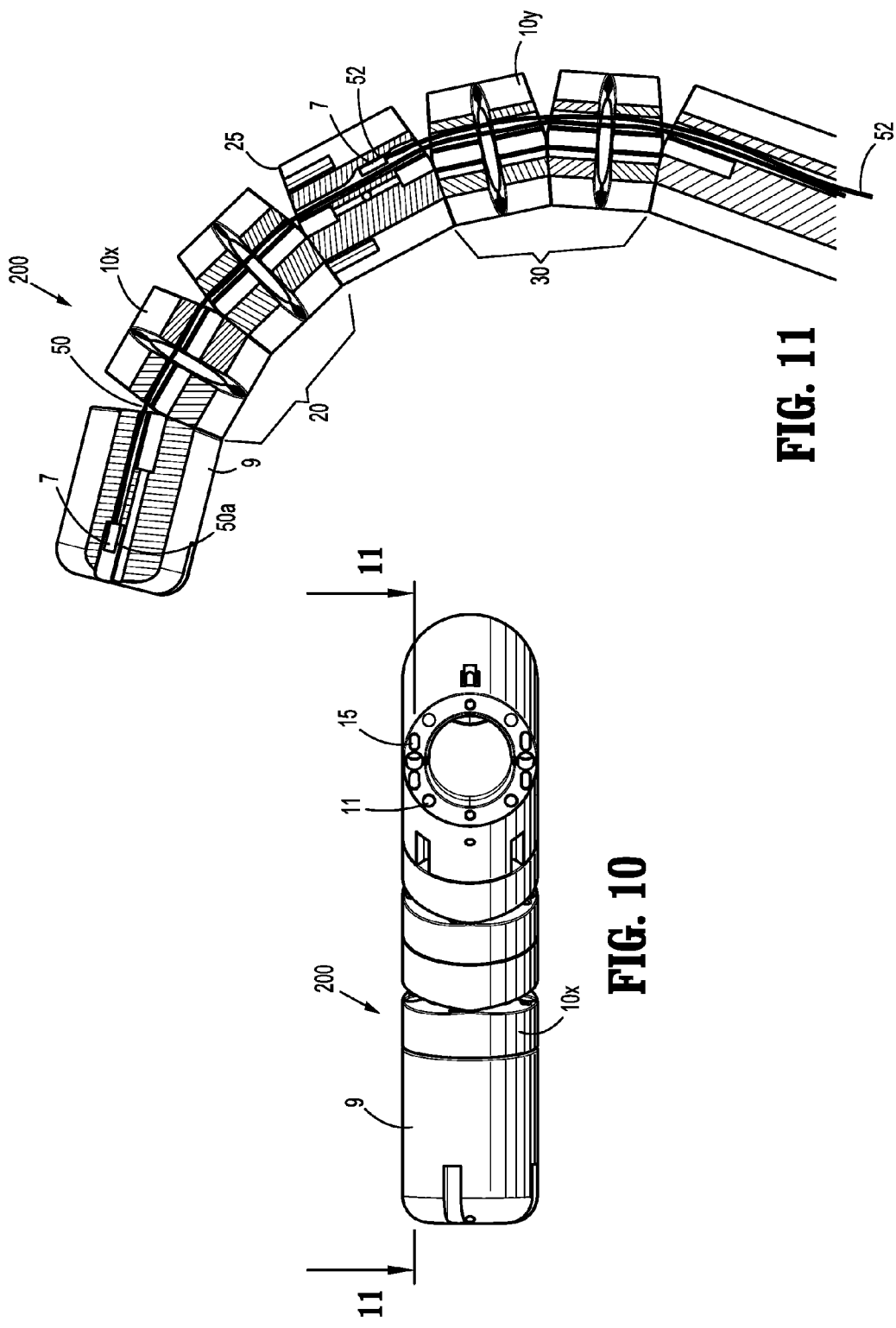

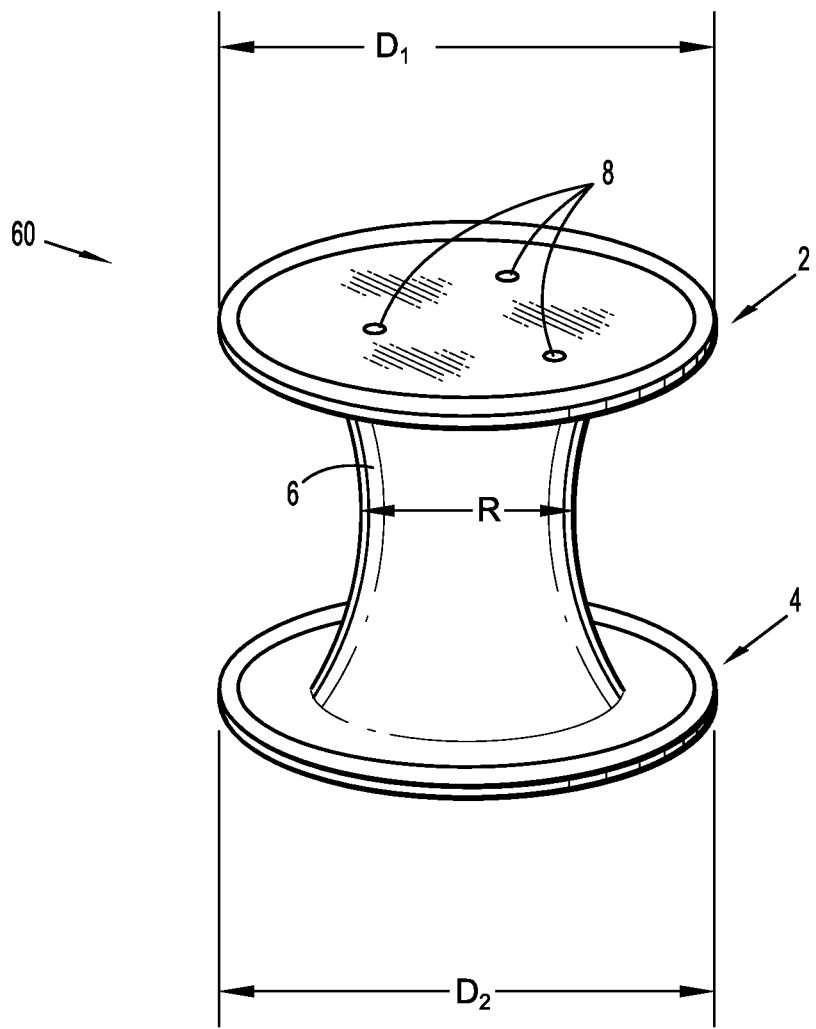
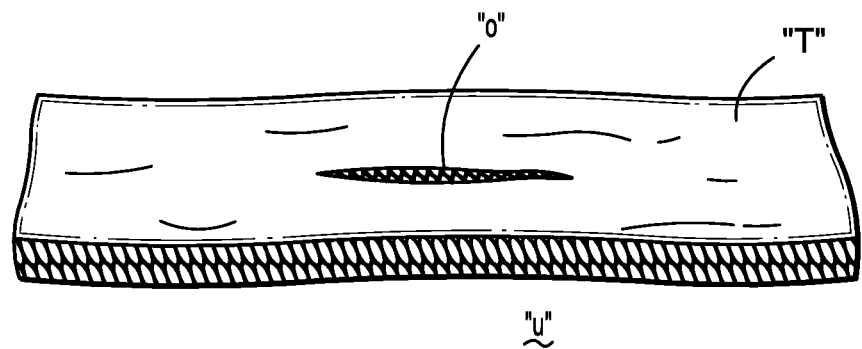
FIG. 17

CONSTANT VALUE GAP STABILIZER FOR ARTICULATING LINKS

CROSS-REFERENCE TO RELATED APPLICATIONS

This application claims the benefit of and priority to U.S. Provisional Patent Application No. 61/814,875, filed Apr. 23, 2013, the entire disclosure of which is incorporated by reference herein.

BACKGROUND

1. Technical Field

The present disclosure relates generally to a surgical instrument including articulating links. More particularly, the present disclosure relates to a surgical instrument including a linkage having reduced positioned error.

2. Background of Related Art

A minimally invasive surgical procedure is one in which a surgeon enters a patient's body through one or more small openings in the patient's skin or naturally occurring openings (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracoscopic surgeries. Advantages of minimally invasive surgical procedures over traditional open surgeries include reduced trauma and recovery time for patients. The disadvantages include the need to insert many instruments through a single opening and a reduced visualization of the surgical site.

It is critical that a surgeon be able to accurately place surgical instruments within the surgical site. Some surgical instruments are configured to articulate. When articulating a surgical instrument, there may be positioning error. In particular, when a surgical instrument includes articulating links, each link may have a positioning error. While the positioning error of each link may be relatively minor, the cumulative effect of all the positioning errors may be significant. Minimizing such positioning error is desirable to facilitate accurate placement of the instruments within the surgical site.

Consequently, a continuing need exists for improved minimally invasive surgical devices.

SUMMARY

Disclosed herein is a surgical instrument for use during a minimally invasive surgical procedure.

The surgical instrument includes a first segment of articulating links and a second segment of articulating links. Positioned between the first and second segments of articulating links is a middle link having a predetermined limited range of rotation. The middle link is positioned between a substantially equal number of articulating links contained in each of the first and second segments. By limiting or controlling the freedom of rotation of the middle link, the positioning error of the distal end of the surgical instrument is reduced.

Positioning error can be reduced by stabilizing the gaps between adjacent articulating links to predictable and generally even values. A gap stabilizer described herein facilitates stabilization of the gaps between the adjacent links. In particular, a surgical instrument is disclosed that includes a plurality of articulating links and is transitionable between a straight and a bent position. The surgical instrument includes at least one gap stabilizer that includes a pair of fluidly connected hydraulic pillows and is positioned on opposite lateral sides of the surgical instrument to provide a correcting moment during bending of the surgical instrument, thereby providing stability to the surgical instrument and facilitating equally dimensioned gaps between the articulating links.

The surgical instrument may include a lumen extending therethrough that is configured and adapted for the reception of a surgical device therethrough. Bending movement of the surgical instrument causes a corresponding bending of the surgical device when the surgical device is placed within the lumen of the surgical instrument. A surgical system includes the surgical instrument described above as well as the surgical device placed within the lumen of the surgical instrument.

A method of using the surgical instrument is also disclosed. The method includes providing a seal anchor member including at least one longitudinally extending port, and placing the seal anchor member within a body opening to access an underlying body cavity. The surgical instrument is placed within the at least one longitudinally extending port and a desired surgical procedure is performed. The surgical device may be placed within the lumen of the surgical instrument. As the surgical instrument is bent during a surgical procedure, the surgical device placed within the surgical instrument is correspondingly bent into a desired orientation. Thereafter, the surgical instrument may be removed from the body opening prior to or at the same time as the seal anchor member. If necessary, the body opening is sealed. For example, an incision may be sealed.

A surgical system may include the surgical instrument, the surgical device, and/or a seal anchor member for positioning within the body opening to access an underlying body cavity.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein:

FIG. 7 is a cross-sectional, side view of the surgical instrument of FIG. 1;

FIG. 8 is a cutaway side view of a middle link;

FIG. 10 is a top view of the surgical instrument of FIG. 9;

FIG. 11 is a cross-sectional side view of the surgical instrument of FIG. 9;

FIG. 17 is a seal anchor member.

DETAILED DESCRIPTION OF THE EMBODIMENTS

Figure 1:
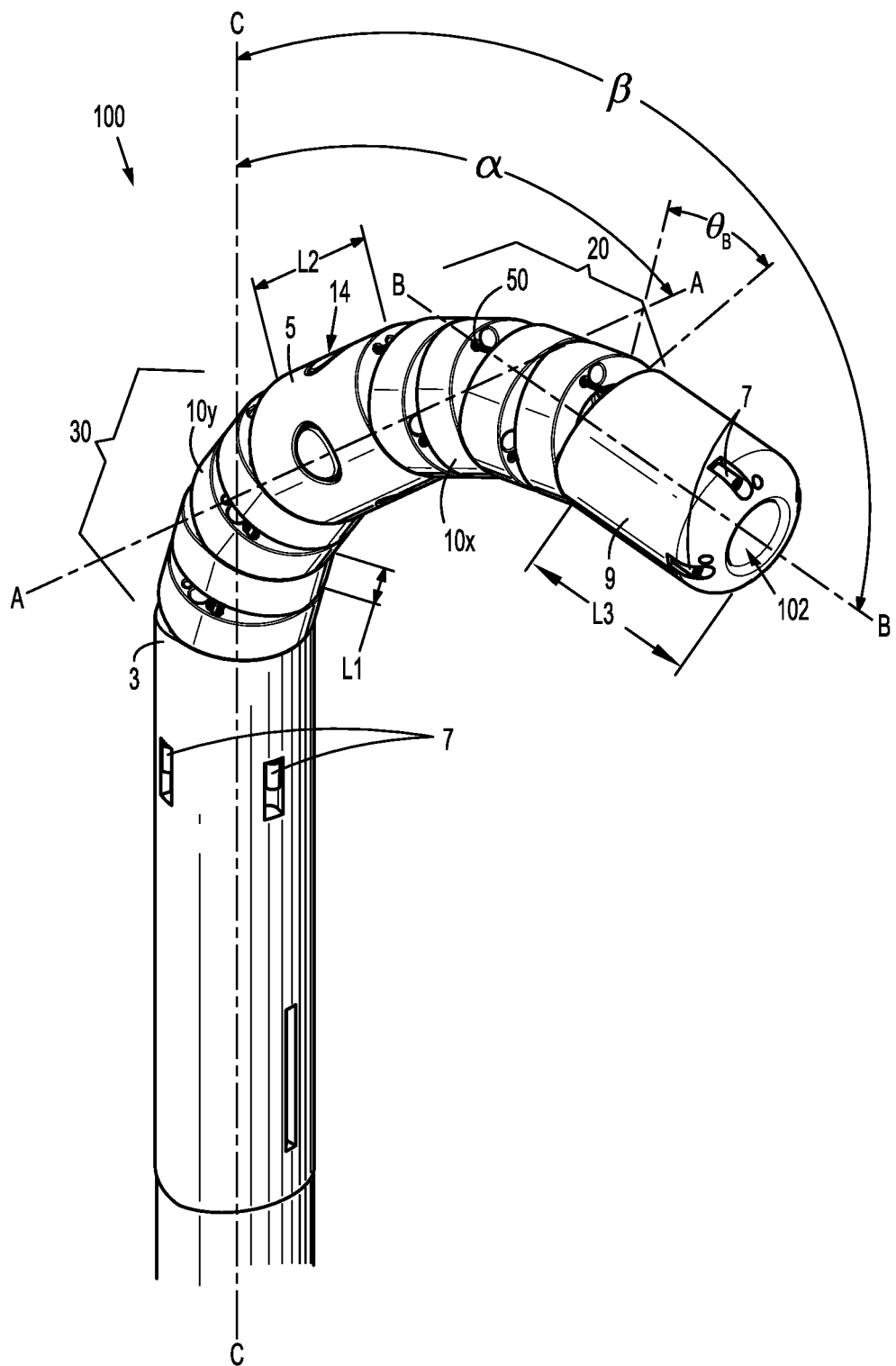
FIG. 1 is a perspective view of an embodiment of a surgical instrument in accordance with the present disclosure and shown in an articulated condition.

Particular embodiments of the present disclosure will be described herein with reference to the accompanying drawings. As shown in the drawings and as described throughout the following descriptions, and as is traditional when referring to relative positioning on an object, the term "proximal" will refer to the end of the apparatus that is closest to the clinician during use, and the term "distal" will refer to the end that is farthest from the clinician during use.

Figure 2:
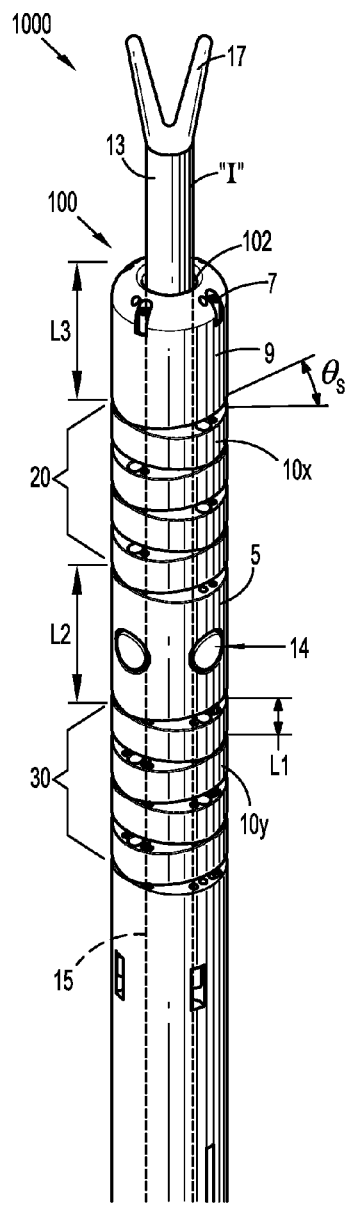
FIG. 2 is a perspective view of a surgical system including the surgical instrument of FIG. 1 shown in a non-articulated position and a surgical device operatively coupled to the surgical instrument.

An embodiment of a surgical instrument will now be described with reference to FIGS. 1-8. A surgical instrument 100 is configured and adapted to transition between an articulated or bent condition (FIG. 1) and a non-articulated or straight condition (FIG. 2). The surgical instrument 100 may include a lumen 102 that extends through the surgical instrument 100 and is configured and adapted to receive a surgical instrument therethrough.

The surgical instrument 100 includes at least two segments including adjacent articulating links 10x, 10y. In particular, a first segment 20 includes a plurality of articulating links 10x and a second segment 30 includes a plurality of articulating links 10y. Each segment 20, 30 may include the same number of articulating links. The first segment 20 is positioned distally relative to the second segment 30 and includes a distal link 9. The distal link 9 may be operatively coupled to an end effector (not shown). A middle link 5 is positioned between the first segment 20 and the second segment 30. Preferably, the first segment 20 and the second segment 30 each include a substantially equal number of links 10x, 10y, respectively. A series of cables 50 pass through the second segment 30 and the first segment 20 and are operatively coupled to the distal link 9 to control the positioning of the distal link 9.

The adjacent links 10x, 10y are shaped and configured to include gaps or spaces between the adjacent links 10x, 10y. The links 10x, 10y contact each other at a contact point 103. The contact point 103 functions as a pivot point for the links 10x, 10y. At the contact points 103, there may be springs 105 (FIG. 7) that bias the surgical instrument 100 toward the unbent or straight position. In particular, each link 10x, 10y may be curved such that the apex of the curve is the contact point 103 between the adjacent links 10x, 10y. The adjacent links 10x, 10y may be arranged such that the contact points 103 are aligned along the same axis such that the gaps between the links 10x, 10y are also aligned co-axially, thereby facilitating bending movement in a single radial direction. In another embodiment, the links 10x, 10y may be arranged and oriented with respect to one another with the contact points 103 alternately aligned, i.e., along a given longitudinal axis, there would be a pattern of a gap followed by a contact point 103, thereby facilitating a bending movement along two radial directions allowing for repositioning to any desired coordinate point. The size of the gap and the value of the angle defined between the gaps is dependent on whether the surgical instrument 100 is bent or straight. As the surgical instrument 100 is bent, the gaps on one side of the surgical instrument will increase while the gaps on the other side of the surgical instrument 100 will decrease.

Figure 3:
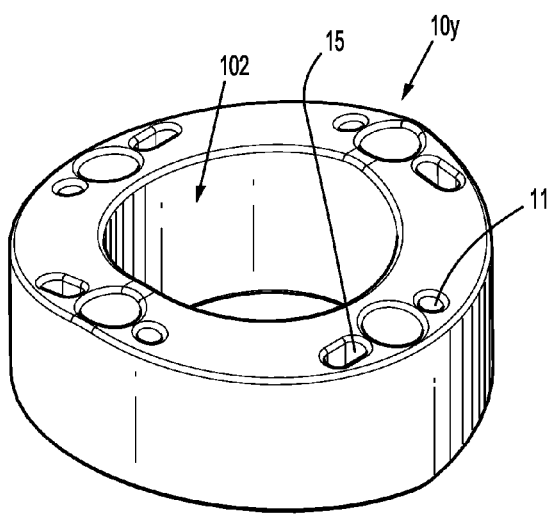
FIG. 3 is a perspective view of an articulating link.
Figure 4:
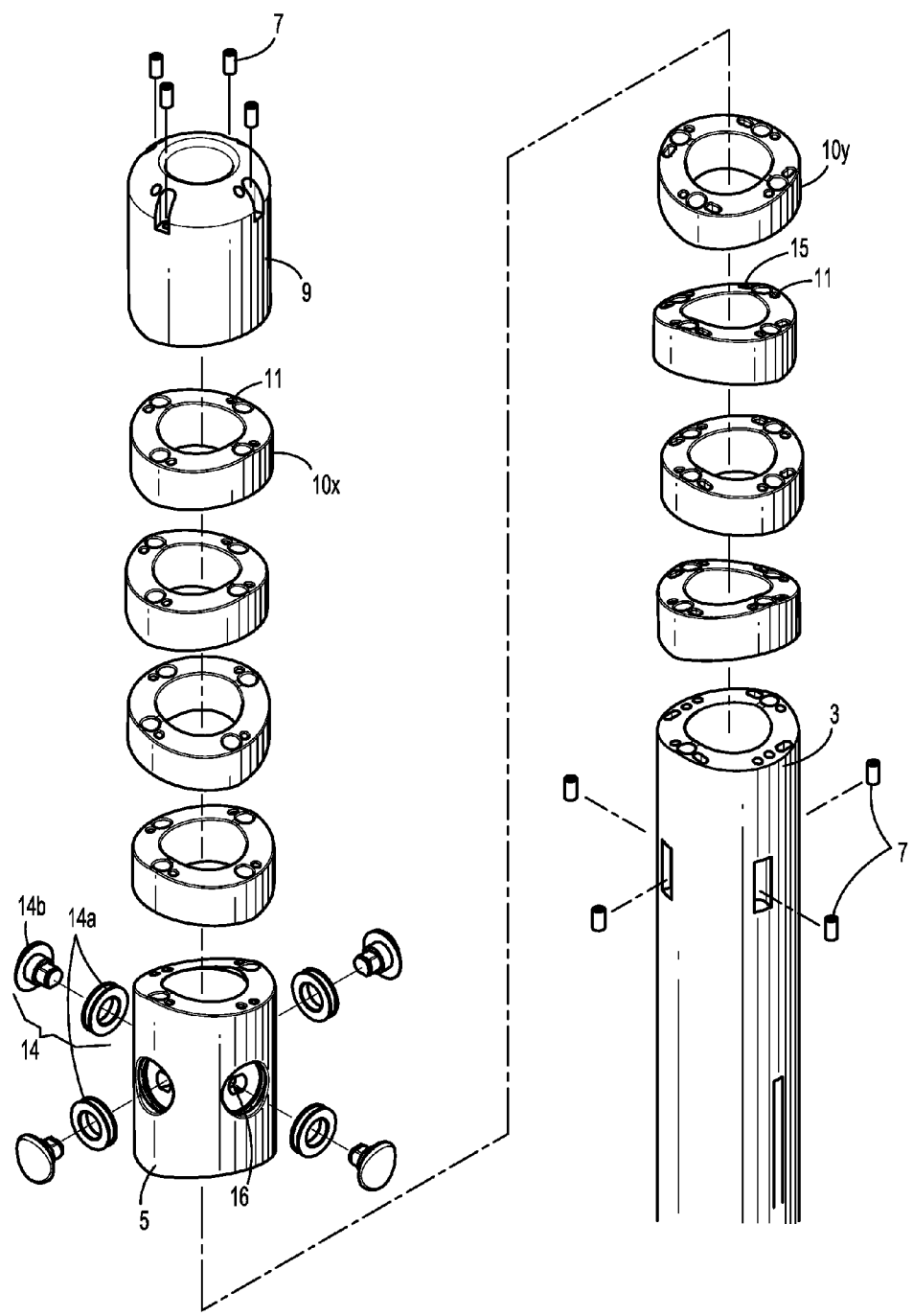
FIG. 4 is an exploded view of the surgical instrument of FIG. 1.
Figure 5:
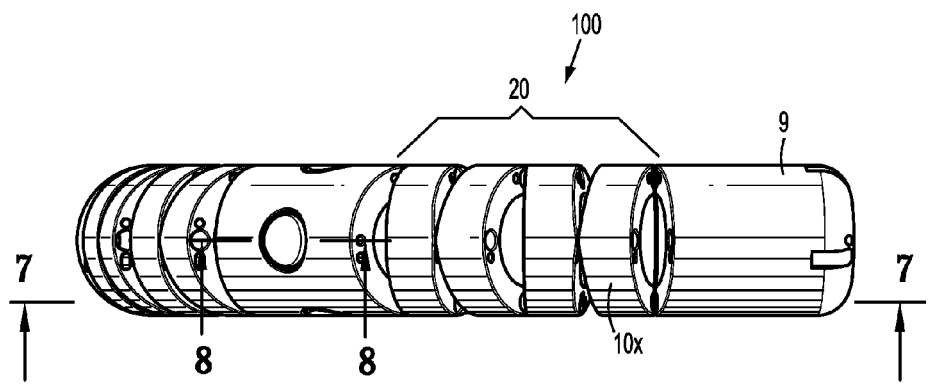
FIG. 5 is a top view of the surgical instrument of FIG. 1.
Figure 6:
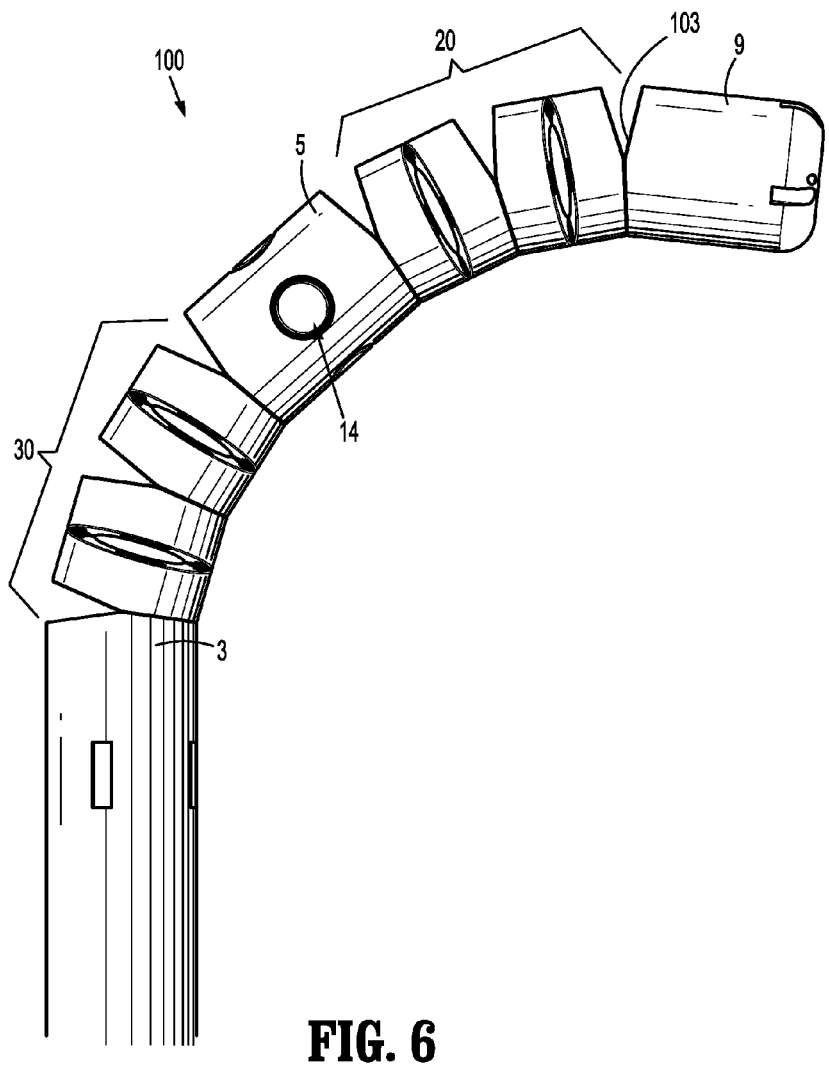
FIG. 6 is a side view of the surgical instrument of FIG. 1 shown in the articulated position.

As shown best in FIG. 3, links 10y of the second segment 30 include a small hole 11 and an elongated hole 15. As shown in FIG. 4, the link 10x includes a small hole 11 for the reception of a single cable, i.e., cable 50. As shown best in FIG. 7, two cables 50, 52 extending from an instrument handle (not shown) pass through each of the elongated holes 15 of links 10y of the surgical instrument 100. Cable 50 only ends through the second segment 30 around a pulley 14a and through small hole 11. The interaction of the cable 52 with the pulley 14a directly controls the position of the middle link 5. In particular, the cable 52 is looped around the pulley 14a which is secured to the middle link 5. The cable 52 is looped around the pulley 14a, effectively doubling the cables acting upon the middle link 5. Application of a force upon the cable 52 in turn applies a force upon the middle link 5, thereby controlling the position of the middle link 5. The middle link 5 may be operatively coupled to several pulleys 14a to facilitate positioning of the middle link 5. For example, the middle link 5 may include four pulleys 14a grouped in generally opposing pairs.

The cable 50 is secured within a distal link 9 adjacent the distal end of the first segment 20. To facilitate radial movement of the distal link 9 in two directions and placement of the distal link 9 at a desired coordinate point, two pairs of opposing cables 50, i.e., four cables 50, may be operatively coupled to the distal link 9. The cable 50 includes a distal end including a ferrule 7 that is secured within a recess 50c defined in the distal link 9. A series of cables 52 only pass through the second segment 30 and are operatively coupled to the middle link 5 to control the positioning of the middle link 5, thereby controlling its freedom of rotation. A first end 52a of the cable 52 is frictionally secured to the base link 3. In particular, the first end 52a of the cable 52 is coupled to a ferrule 7 that is secured within a recess 52c within the base link 3. A second end 52a of the cable 52a and a second end 50a of the cable 50a may extend to a handle (not shown). Application of a force upon the second ends 50a, 52a of cables 50a, 50b, respectively, result in a force being applied to the distal link 9 and the base link 3, respectively.

The middle link 5 may include a plurality of pulley systems 14 that control the actuation of the surgical instrument 100. As shown in FIG. 4 the surgical instrument 100 includes four pulley systems 14. The pulley system 14 includes a pulley 14a around which the cable 52 is looped, and a pin 14b that is frictionally receivable within a recess 16. The pulley systems 14 are positioned in a juxtaposed relationship with one another such that when a force is applied to one of the pulley systems 14, an opposite force can subsequently be applied to a pulley system 14 positioned opposite to bring the second segment 30 surgical instrument 100 back to the original position. Since separate groups of cables 50, 52 are operatively coupled to the distal link 9 and middle link 5, respectively, the first and second segments 20, 30, respectively, are independently actuatable. The cables 50, 52 move together and the pulley system 14 facilitates maintaining a ratio of two to one for the displacement of the distal link 9 relative to the middle link 5. In particular, a force is applied to both the ends 50b, 52b of cables 50, 52, respectively, causing the pair of cables 50, 52 to move together. The positioning of the pulley system 14 with respect to the middle link 5 and the interaction of the cable 52 and the pulley 14a creates the necessary difference in the displacement between the distal link 9 and the middle link 5 to maintain a displacement ratio of 2:1.

By controlling the movement of the middle link 5 relative to the second segment 30, the positioning error of the distal link 9 is minimized. As shown in FIG. 1, the base link 3 defines a longitudinal axis C, the middle link 5 defines a longitudinal axis A, and the distal link 9 defines a longitudinal axis B. The longitudinal axis A of the middle link 5 and the longitudinal axis C of the base link 3 define an angle α therebetween. In addition, the longitudinal axis B of the distal link 9 and the longitudinal axis C of base link 3 define an angle β therebetween. In an embodiment, the middle link 5 is generally evenly centered between the segments 20, 30, and the angle α defined between the middle link 5 and the base link 3 is roughly twice the value as compared to the angle β defined between the distal link 9 and the base link 3 for values of angle β that are between 0° and 96°. In addition, in an embodiment, the angle $\theta_s$ between the planes defined by the surfaces of links 10x, 10y as measured at the contact point 103 when the surgical instrument 100 is straight is approximately 16°. The value of the angle $\theta_B$ when the surgical instrument 100 is bent is the difference of the angle $\theta_s$ (angle between links 10x, 10y when straight) multiplied by the number of gaps and the angle β defined between the longitudinal axis B of the distal link 9 and the longitudinal axis C of the base link 3 divided by the number of gaps.

When the surgical instrument 100 is in an extreme position, as in maximally bent, the positioning error is at a minimum. In the maximally bent position, angle β is 96° and angle α is 48°, and the positioning error is zero. When the gaps between the links 10x, 10y are equal, the positioning error is at the theoretical minimum. In particular, when the surgical instrument 100 is bent, the sum of the gaps on one side of the surgical instrument 100 is the sum of the maximum angle β (the angle defined between the longitudinal axis B of the distal link 9 and the longitudinal axis C of the base link 3), i.e., 96°, and the actual angle β (the angle defined between the longitudinal axis B of the distal link 9 and the longitudinal axis C of the base link 3). Each link 10x, 10y has a length $L_1$ that in an embodiment is equal to 0.4000, the middle link 5 has a length $L_2$ that is equal to 0.8453, and the distal link 9 has a length that is equal to On the other side of the surgical instrument 100, the sum of the gaps is the difference of the maximum angle β, i.e., 96°, and the actual angle β. Where there are six (6) gaps between the links 10x, 10y, the Cartesian coordinates, i.e., x and y coordinates, of the theoretical position distal link 9 is given by the following equations: the x-coordinate=$L_1*\sin(\beta/6)+L_1*\sin((2*\beta)/6)+L_2*\sin((3*\beta)/6)+L_1*(\sin((4*\beta)/6)+L_1*\sin((5*\beta)/6)+L_3*\sin(\beta)$ and the y-coordinate=$L_1*\cos(\beta/6)+L_1*\cos((2*\beta)/6)+L_2*\cos((3*\beta)/6)+L_1*(\cos((4*\beta)/6)+L_1*\sin((5*\beta)/6)+L_3*\cos(\beta)$. The actual position of the distal link 9 for values of β that are between 0° and 32°, the x and y coordinates are determined by the following equations: $x_1=L_1*\sin(16)+L_1*\sin(16+\beta/2)+L_2*\sin(\beta/2)+L_1*\sin(\beta/2+16)+L_1*\sin(\beta/2+16+\beta/2)+L_3*\sin(\beta)$ and $y_1=L_1*\cos(16)+L_1*\cos(16+\beta/2)+L_2*\cos(\beta/2)+L_1*\cos(\beta/2+16)+L_1*\cos(\beta/2+16+\beta/2)+L_3*\cos(\beta)$. The actual position of the distal link 9 for values of β that are between 32° and 96°, the x and y coordinates are determined by the following equations: $x_2=L_1*\sin(16)+L_1*\sin(32)+L_2*\sin(\beta/2)+L_1*\sin(\beta/2+16)+L_1*\sin(\beta/2+32)+L_3*\sin(\beta)$ and $y_2=L_1*\cos(16)+L_1*\cos(32)+L_2*\cos(\beta/2)+L_1*\cos(\beta/2+16)+L_1*\cos(\beta/2+32)+L_3*\cos(\beta)$. The positioning error is determined calculating the difference between the actual position and the theoretical position, i.e., the absolute value of the square root of the sum of the difference of the theoretical x-coordinate and the actual x-coordinate squared and the difference of the theoretical y-coordinate and the actual y-coordinate squared (i.e., $|\sqrt{((x-x_1)^2+((y-y_1)^2)}|$). In particular, for β=0°, the positioning error is 0.4453, for β=48°, the positioning error is 0.3253, and for β=96°, the positioning error is 0.0000.

When the middle link 5 is positioned between segments of articulating links that have a roughly even number of equally sized links, the positioning error is less than it would be otherwise. In particular, as discussed above, when the surgical instrument is straight, and the movement of the middle link 5 is constrained, angle α and angle β are zero and the maximum positioning error is 0.4453.

However, if the middle link 5 had an unrestricted freedom of movement and was free to rotate, the gaps between the links 10x, 10y would be cumulated in the first segment 20 and the maximum positioning error would be the sum of all of the positioning errors of each link 10x, 10y, and the maximum positioning error would be 1.3440. This is because the gaps between the links 10x contained in the first segment 20 and the gaps between the links 10y contained in the second segment would not have the same value. In addition, the value of angle α would not be equal to half the value of angle β. However, by constraining the movement of the middle link 5, the positioning error of the distal link 9 is greatly reduced since the position of the middle link 5 is not dependent upon the position of adjacent links 10x, 10y and therefore there will not be a cumulative error effect upon the middle link 5.

Figure 9:
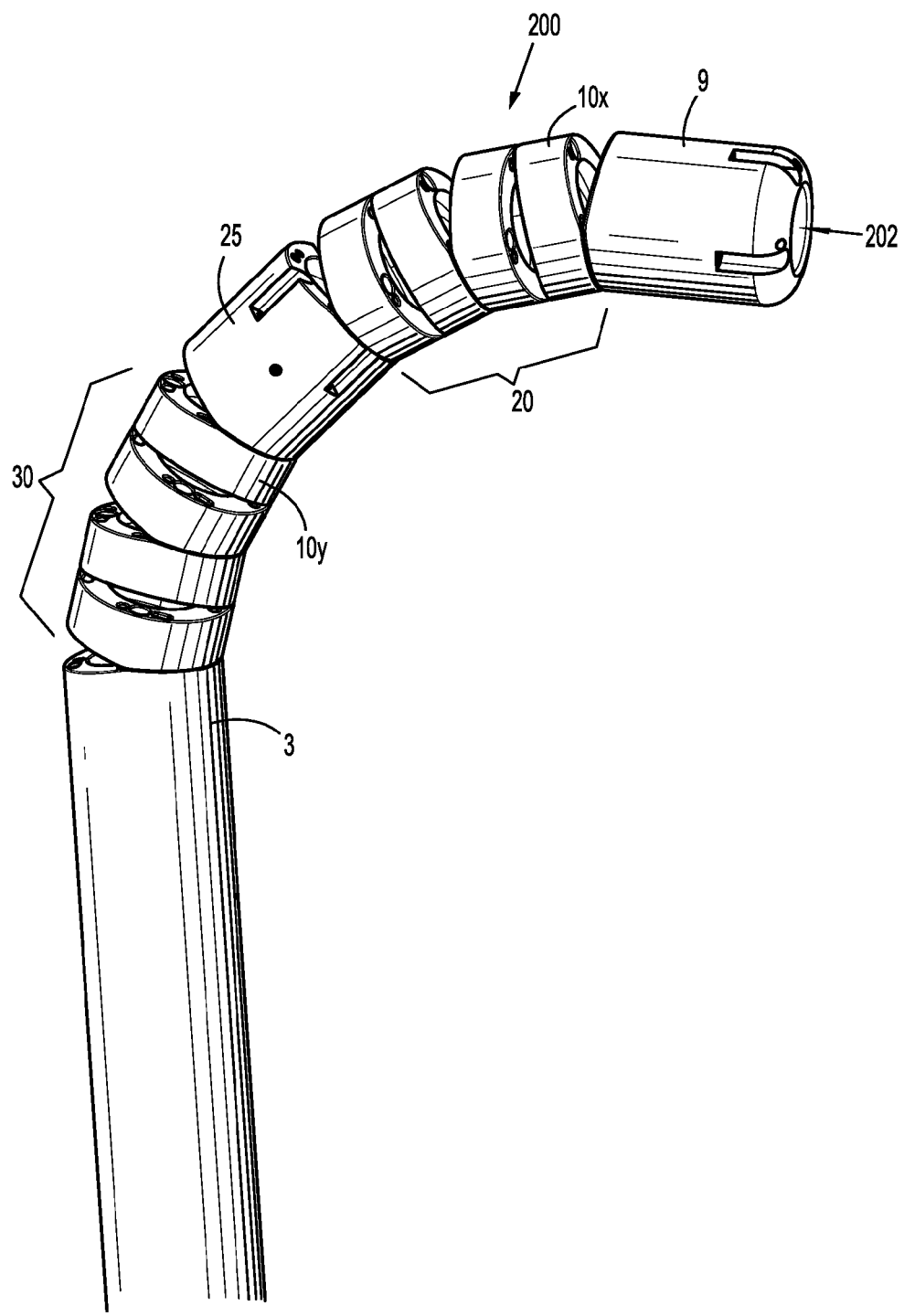
FIG. 9 is a perspective view of an embodiment of a surgical instrument shown in an articulated position.

In another embodiment, a surgical instrument 200 does not include a pulley system to effect actuation of the surgical instrument 200. Surgical instrument 200 will now be described with reference to FIGS. 9-11. The surgical instrument 200 is similar to the surgical instrument 100 except that it includes middle link 25 instead of middle link 5. In particular, surgical instrument 200 does not utilize a pulley system. As shown best in FIG. 11, the surgical instrument 200 includes two cables 50, 52 on a lateral side of the surgical instrument 200, e.g., on each of four lateral sides, to facilitate displacement of the surgical instrument to any desired three-dimensional coordinate point. The first cable 50 extends through a first segment 20 of articulating links 10x and a second segment 30 of articulating links 10y and is secured to distal link 9. The second cable 52 extends through the second segment 30 of articulating links 10y and terminates and is secured to the middle link 25. The cables 50, 52 are configured and adapted to displace the distal link 9 relative to the middle link 25 in a ratio of two to one. In particular, the cable 50 that extends to the distal link 9 will move twice as fast as the cable 52 that only extends to the middle link 25 thereby facilitating displacement of the distal link 9 in a two to one ratio relative to the middle link 25. A longitudinally extending lumen 202 extends through the surgical instrument 200.

Another embodiment of a surgical instrument will now be described with reference to FIGS. 12-16. Surgical instrument 300 includes the features of the surgical instrument 100 and additionally includes the following features that will now be described. A longitudinal lumen 302 extends through the surgical instrument 300. Additionally the surgical instrument 300 includes hydraulic gap stabilizers 350 (FIGS. 13-14) that are configured and adapted to provide stability to the surgical instrument 300 by providing a corrective moment.

Figure 12:
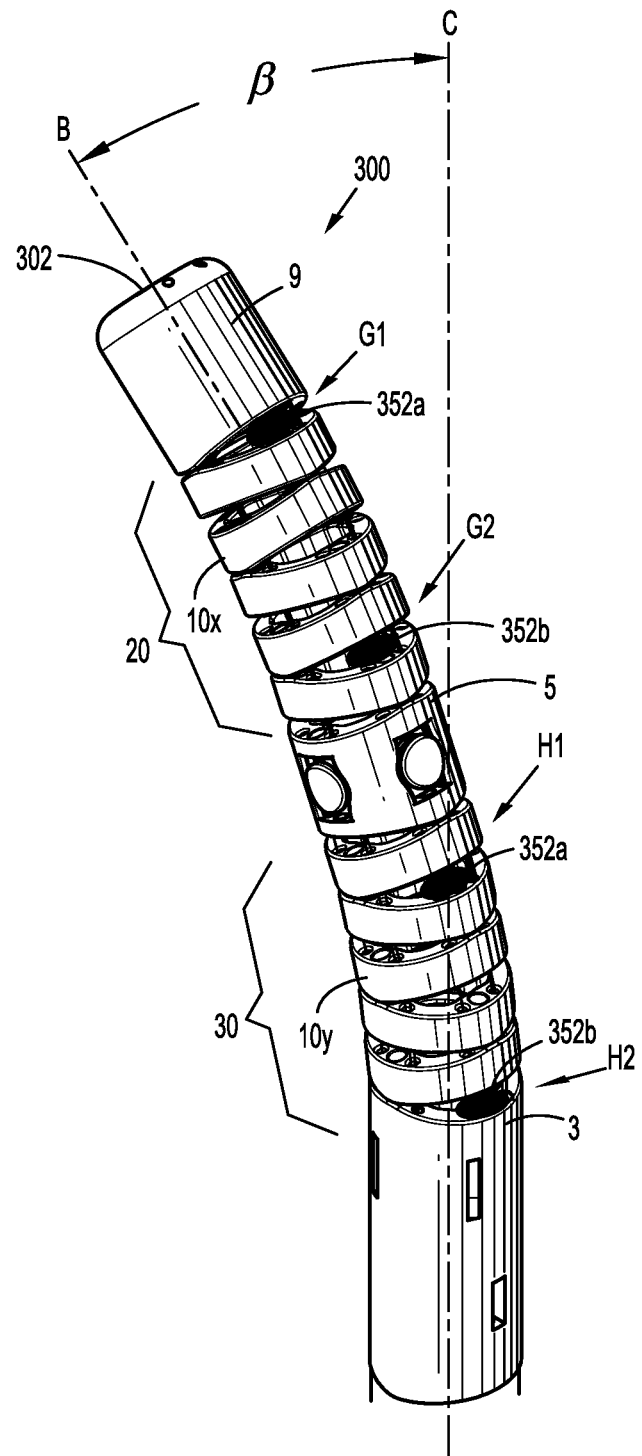
FIG. 12 is a perspective view of an embodiment of a surgical instrument in accordance with the present disclosure.
Figure 14:
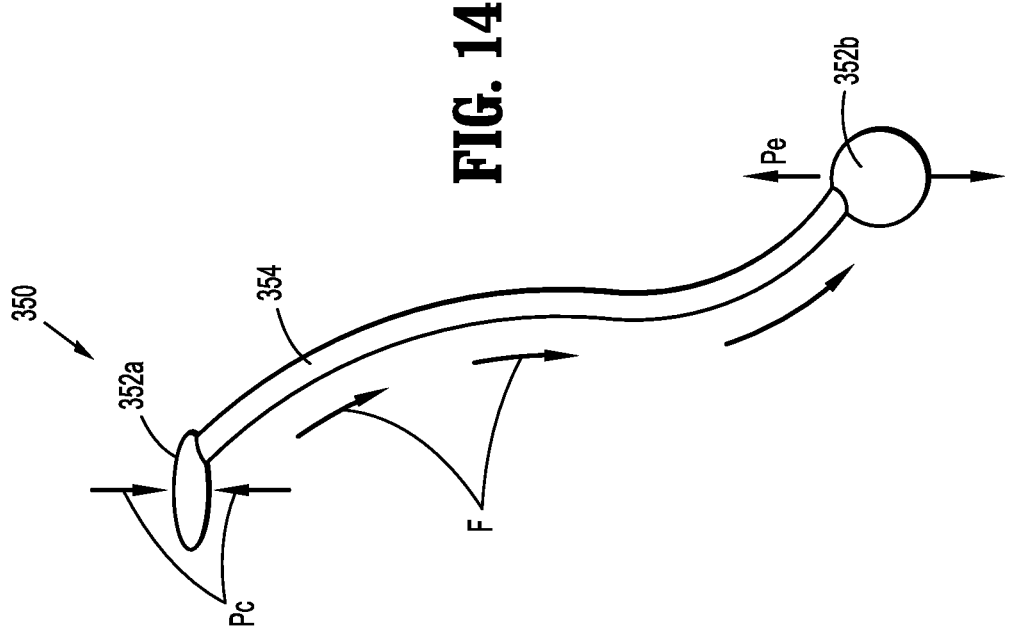
FIG. 14 is a perspective view of a gap stabilizer in a second condition.
Figure 13:
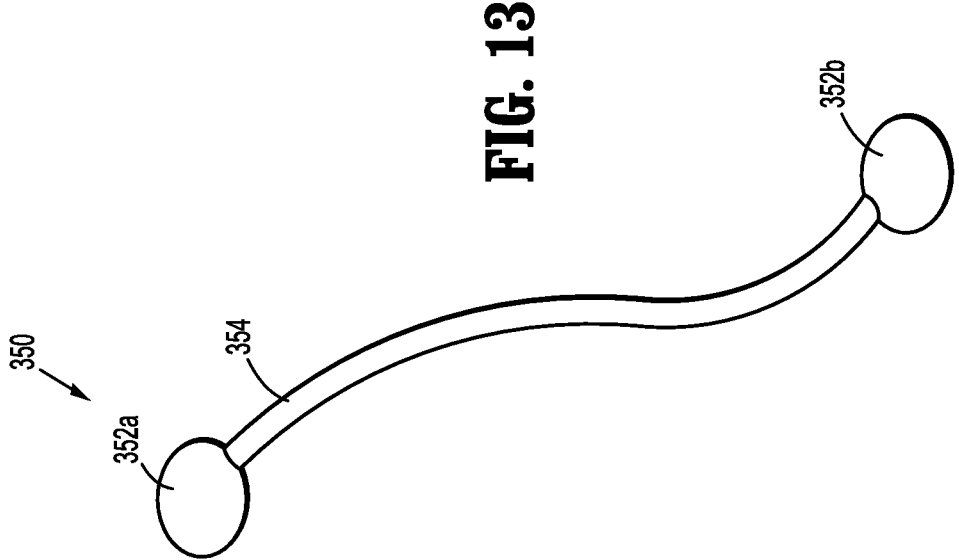
FIG. 13 is a perspective view of a gap stabilizer in a first condition.

As shown best in FIGS. 13 and 14, the hydraulic gap stabilizer 350 includes hydraulic pillows 352a, 352b that are configured and adapted to contain a fluid therein. The hydraulic pillows 352a, 352b are fluidly connected by a fluid conduit 354. Each of the hydraulic pillows 352a, 352b may be configured and adapted to retain a given amount of fluid unless acted upon by a force. The volume of the fluid contained within the gap stabilizer 350 is constant. As shown in FIG. 14, application of a compressive force Pc to the hydraulic pillow 352a urges a fluid flow F away from the compressed hydraulic pillow 352a toward the hydraulic pillow 352b thereby exerting an expanding force Pe upon the hydraulic pillow 352b, thereby causing the hydraulic pillow 352a to decrease in size and the hydraulic pillow 352b to increase in size. Conversely, application of a compressive force upon hydraulic pillow 352b would result in fluid flow F away from the hydraulic pillow 352b toward the hydraulic pillow 352a causing a reduction in the size of the hydraulic pillow 352b and an increase in the size of the hydraulic pillow 352a. The volume of the fluid within the gap stabilizer 350 is constant, and the volume of fluid contained within each of the hydraulic pillows 352a, 352b is a function of angle β (FIG. 12), i.e., the angle between the longitudinal axis C of the base link 3 and the longitudinal axis B of the distal link 9.

Accordingly, as the hydraulic pillows 352a, 352b fill the spaces defined by opposing sides of gaps G1, G2, H1, and H2 along opposing lateral sides of the surgical instrument 300 and maintain the range of motion through which adjacent links 10x, 10y pivot relative to one another. As the hydraulic pillows 352a, 352b transfer a constant fluid volume therebetween, as adjacent links 10x, 10y pivot relative to each other, the sum angle and sum volume defined between opposing sides of gaps G1, G2, H1, and H2 along opposing lateral sides of the surgical instrument 300 remains constant. In this controlled manner, gap stabilizers 350 operate to eliminate positioning error at the distal end of surgical instrument 300.

As shown in FIG. 12, pairs of hydraulic stabilizers 350 may be placed along intersecting planes such that the hydraulic pillows 352a, 352b are placed along opposing lateral side of the surgical instrument 300 between the first gaps G1, H1 of the first and second segments 20, 30, respectively, and between the last gaps G2, H2 of the first and second segments 20, 30, respectively. It should be noted that while a first set of hydraulic pillows 352a, 352b are shown placed along opposing lateral sides of the surgical instrument 300 to effect articulation along a first plane of articulation, a second set of hydraulic pillows 352a, 352b may be placed along other opposing lateral sides of the surgical instrument 300 to effect articulation in a different, second plane of articulation. In embodiments, the first and second planes of articulation may be transverse to one another. One skilled in the art of the present disclosure will envision other suitable arrangements of hydraulic pillows 352a, 352b.

Figure 16:
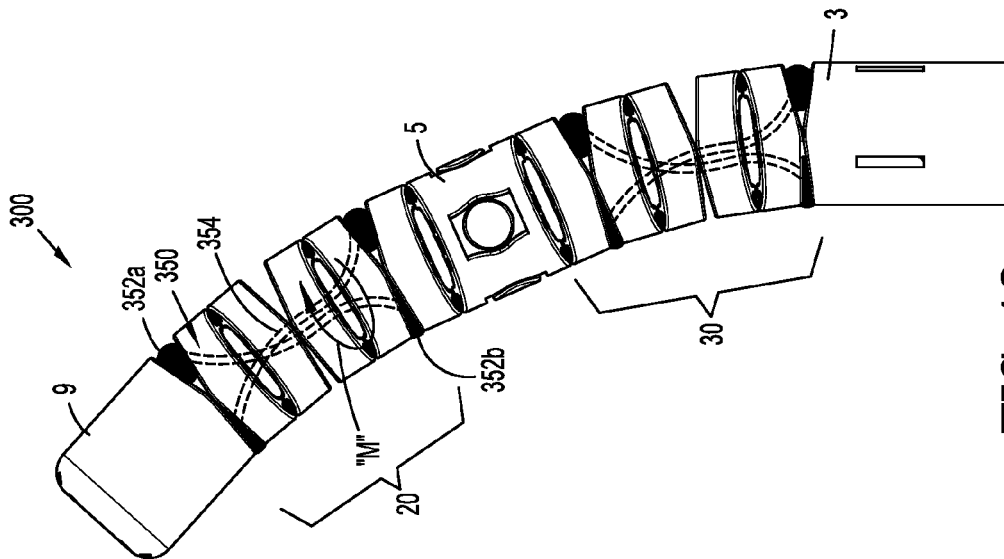
FIG. 16 is a perspective view of the surgical instrument of FIG. 15 shown in a second condition.
Figure 15:
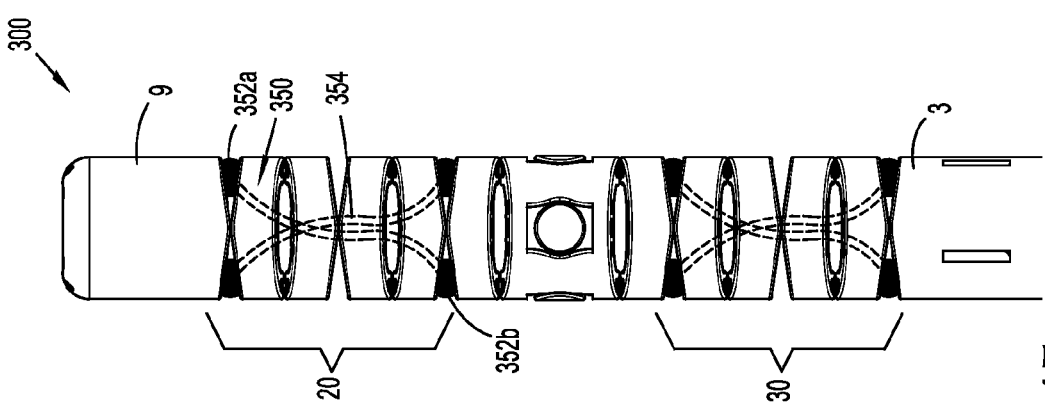
FIG. 15 is a perspective view of the surgical instrument of FIG. 12 shown in a first condition.

As shown in FIG. 15, in the straight position, the gaps between the links 10x, 10y are substantially the same on all sides of the instrument, and the size of the hydraulic pillows 352a, 352b and the fluid contained therein are substantially the same. As shown in FIG. 16, the placement of the hydraulic stabilizers 350 and the fluid flow F therein provides a corrective moment "M" to stabilize the surgical instrument 300, which keeps the gaps from collapsing upon bending of the surgical instrument 300 during bending of the surgical instrument 300. The corrective moment may resist or smooth the transitioning of the surgical instrument between the straight and bent positions. During bending, the hydraulic pillows 352a, 352b help maintain substantially equal gaps between links 10x, 10y within each segment 20, 30. Moreover, by placing the hydraulic pillows 352a, 352b in opposing gaps of pressure points, the gaps between the articulating links 10x, 10y are stabilized. By providing a force in opposition to the rotation of the articulating links 10x, 10y the freedom of rotation for the articulating links 10x, 10y is reduced, thereby facilitating stability and precise positioning of the instrument 300.

During use a minimally invasive surgery, a surgeon may place a seal anchor member 60 (FIG. 17) within a body opening "O" defined in tissue "T". The body opening "O" may be naturally occurring (e.g., mouth, anus, vagina) or an incision. The seal anchor member includes a trailing end 2, a leading end 4, and an intermediate section 6. The trailing end 2 defines a diameter $D_1$, the leading end defines a diameter $D_2$, and the intermediate section 6 defines a radial dimension that varies along the longitudinal length of the seal anchor member to define a substantially hour-glass shape. The hour-glass configuration of the seal anchor member 60 facilitates the securing of the seal anchor member 60 within the body opening "O" to access an underlying body cavity "U". Extending longitudinally through the seal anchor member 60 are one or more ports 8 that are configured and adapted for the substantially sealed reception of surgical instruments. An example of a seal anchor member 60 is described in U.S. Pat. Pub. 2009/0093752, the contents of which are hereby incorporated by reference in its entirety.

The surgical instruments 100-300 are configured and adapted to be placed within the ports 8 of the seal anchor member 60 that is placed within the body opening "O" of tissue "T". The seal anchor member 60 is placed within a body opening to access an underlying body cavity. Optionally, the surgical instrument 100-300 is placed within one of the ports 8 prior to or at the same time as the seal anchor member 60 is anchored within the body opening "O". Depending on the desired surgical procedure, a particular end effector (not shown) may be operatively coupled to the distal link 9 of the surgical instruments 100-300. The end effector chosen is determined based upon the particular application. As discussed above, the positioning of the distal link 9, and the end effector secured thereto, is facilitated by the application of force upon cables 50, 52. The independent actuation of these cables 50, 52 facilitates positioning of the distal link 9 and the end effector, thereby facilitating proper placement of the surgical instrument 100-300 with respect to the target body structures within the body opening "O". Once the desired surgical procedure is completed, the surgical instrument 100-300 and the seal anchor member 60 are removed from the body opening "O". If necessary, the body opening "O" is sealed, e.g., stapled or stitched.

As shown in FIG. 2, a surgical system 1000 includes surgical instrument 100 and a surgical device "I" that is operatively coupled to the surgical instrument 100. As discussed above, the surgical instrument 100-300, each includes lumen 102, 202, 302 extending longitudinally therethrough and including both distal and proximal openings. A surgical device "I" may be placed within the lumen 102-302, as will now be described with respect to the surgical instrument 100. As shown in FIG. 2, the lumen 102 may receive a surgical device "I" therein or therethrough. The surgical device "I" includes a distal end 13 and a proximal end 15. A suitable end effector 17 may be operatively coupled to the surgical device "I". An actuator (not shown) may be operatively coupled to the proximal end 15 of the surgical device "I" to cause actuation of the end effector 17. The surgical device "I" is configured and adapted to have a contour or shape that dynamically adjusts to that that of the lumen 102 in which the surgical device "I" is positioned. For example, the surgical device "I" may be formed from a complaint or flexible material or a material having shape memory properties, or may include a plurality of articulating links such that the surgical device "I" may be bent, shaped, or contoured in response to a corresponding movement of the surgical instrument 100-300. During use, the surgeon may place the surgical instrument 100-300 into one of the ports 8 of the seal anchor member 60, and then may place the surgical device "I" through the lumen 102, 202, 302 of the surgical instrument 100-300. The surgeon may alternatively place the surgical system 1000 in an already assembled condition into one of the ports 8 of the seal anchor member 60 or the surgical system 1000 and the seal anchor member 60 may be placed within the body opening "O" at the same time.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical instrument comprising:
    at least one segment having a plurality of articulating links defining gaps therebetween, the at least one segment transitionable between a straight position and a bent position; and
    at least one gap stabilizer including a first hydraulic pillow and a second hydraulic pillow that are in fluid communication with one another, the gap stabilizer containing a constant volume of fluid that is transferable between the first and second hydraulic pillows, wherein the first and second hydraulic pillows are positioned within the gaps defined by the articulating links along opposing lateral sides of the at least one segment to provide stability to the surgical instrument during transitioning of the at least one segment to the bent position.

2. The surgical instrument of claim 1, wherein bending of the surgical instrument results in a corrective moment to stabilize the surgical instrument.

3. The surgical instrument of claim 1, wherein the corrective moment resists transitioning of the surgical instrument between the straight and bent positions.

4. The surgical instrument of claim 1, wherein transitioning of the at least one segment to the bent position causes the first hydraulic pillow to compress and second hydraulic pillow to expand on opposing lateral sides of the at least one segment.

5. The surgical instrument of claim 4, wherein compression of the first hydraulic pillow and expansion of the second hydraulic pillow provides a corrective moment.

6. The surgical instrument of claim 4, wherein fluid flows from the hydraulic pillow that is compressed to the hydraulic pillow that is expanded.

7. The surgical instrument of claim 4, wherein the at least one gap stabilizer facilitates maintaining evenly dimensioned gaps between the articulating links.

8. The surgical instrument of claim 1, wherein a lumen extends longitudinally therethrough.

9. The surgical instrument of claim 1, wherein the lumen is configured to receive a surgical device therethrough.

10. A surgical system comprising:
    a surgical instrument including:
        at least one segment having a plurality of articulating links defining gaps therebetween, the at least one segment transitionable between a straight position and a bent position, wherein a lumen extends longitudinally through the at least one segment; and
        at least one gap stabilizer including a first hydraulic pillow and a second hydraulic pillow that are in fluid communication with one another, the gap stabilizer containing a constant volume of fluid that is transferable between the first and second hydraulic pillows, wherein the first and second hydraulic pillows are positioned within the gaps defined by the articulating links along opposing lateral sides of the at least one segment to provide stability to the surgical instrument during transitioning of the at least one segment to the bent position; and
    a surgical device, the surgical device receivable within the lumen, there surgical device defining a first contour, wherein the lumen defines a second contour, and wherein the first contour of the surgical device corresponds to the second contour of the lumen.

11. The surgical system of claim 10 further comprising a seal access member for positioning within a body opening for accessing an underlying body cavity.

12. A method for performing a surgical procedure comprising:
    providing a surgical instrument including:
        at least one segment having a plurality of articulating links defining gaps therebetween, the at least one segment transitionable between a straight position and a bent position; and
        at least one gap stabilizer including a first hydraulic pillow and a second hydraulic pillow that are in fluid communication with one another, the gap stabilizer containing a constant volume of fluid that is transferable between the first and second hydraulic pillows, wherein the first and second hydraulic pillows are positioned within the gaps defined by the articulating links along opposing lateral sides of the at least one segment to provide stability to the surgical instrument during transitioning of the at least one segment to the bent position;
    providing a seal anchor member positionable within a body opening to access an underlying body cavity;
    placing the seal anchor member within the body opening, the seal anchor member including at least one longitudinally extending port;
    placing the surgical instrument through the at least one longitudinally extending port to access the underlying body cavity;
    performing a desired surgical procedure;
    removing the surgical instrument from the body cavity; and
    removing the seal anchor member.

13. The method for performing a surgical procedure of claim 12, wherein the surgical instrument defines a lumen extending therethrough.

14. The method for performing a surgical procedure of claim 13, further comprising placing a surgical device through the lumen of the surgical instrument.

15. The method for performing a surgical procedure of claim 14, wherein bending movement of the surgical instrument results in a corresponding bending movement of the surgical device when the surgical device is placed within the lumen of the surgical instrument.

* * * * *